(12) United States Patent
Hahn et al.

(10) Patent No.: US 7,238,521 B2
(45) Date of Patent: Jul. 3, 2007

(54) MICROARRAY HYBRIDIZATION DEVICE HAVING BUBBLE-FRACTURING ELEMENTS

(75) Inventors: Soonkap Hahn, San Clemente, CA (US); Jhobe Steadman, San Diego, CA (US); Pavel Tsinberg, San Diego, CA (US); Tim Watanaskul, Oceanside, CA (US); Yehudit Gerassi, San Diego, CA (US)

(73) Assignee: Biocept, Inc., San Diego, CA (US)

( * ) Notice: Subject to any disclaimer, the term of this patent is extended or adjusted under 35 U.S.C. 154(b) by 476 days.

(21) Appl. No.: 10/722,290

(22) Filed: Nov. 24, 2003

(65) Prior Publication Data

US 2005/0112589 A1    May 26, 2005

(51) Int. Cl.
*C12M 3/00* (2006.01)
*C12M 1/00* (2006.01)
*C12Q 1/68* (2006.01)
*C01N 15/06* (2006.01)
*C01N 33/48* (2006.01)

(52) U.S. Cl. .................. 435/288.2; 435/6; 435/283.1; 435/287.2; 422/68.1

(58) Field of Classification Search .............. 435/288.2
See application file for complete search history.

(56) References Cited

U.S. PATENT DOCUMENTS

| | | | |
|---|---|---|---|
| 4,750,556 A | * | 6/1988 | del Valle P. et al. ........ 165/169 |
| 5,910,288 A | | 6/1999 | Schembri |
| 5,922,591 A | * | 7/1999 | Anderson et al. ........ 435/287.2 |
| 6,186,659 B1 | | 2/2001 | Schembri ................... 366/262 |
| 6,258,593 B1 | | 7/2001 | Schembri et al. ........ 435/287.2 |
| 6,420,114 B1 | | 7/2002 | Bedilion et al. | 
| 6,485,918 B1 | | 11/2002 | Schermer et al. |

(Continued)

FOREIGN PATENT DOCUMENTS

FR           2697913 A1     5/1994
WO        WO99/36576    *  7/1999

OTHER PUBLICATIONS

Aldrich Techware Catalog (Sigma-Aldrich, St. Louis, MO p. 181 (1995-1996).*

(Continued)

*Primary Examiner*—Ram R. Shukla
*Assistant Examiner*—Robert T. Crow
(74) *Attorney, Agent, or Firm*—Fitch, Even, Tabin & Flannery

(57) ABSTRACT

A novel hybridization device that improves the efficiency and consistency of microarray hybridization reactions by achieving a greater degree of internal mixing of target solution. The device provides a gasket-and-cover-type chamber wherein solution mixing is achieved by the creation of a multitude of microbubbles. One or more of the inner walls that define the chamber contain bubble-rupturing elements that extend into the chamber and terminate in sharp edges. They are typically located on opposite sides of a rectangular chamber and are pointed in a direction opposing bubble movement. Their interference with larger bubbles causes their breakup into microbubbles which travel separate and distinct paths as a result of external agitation and thereby provide improved solution mixing that results in a uniform distribution of target molecules to the probe molecules bound to the substrate. The sensitivity and consistency of the hybridization reaction is significantly increased.

22 Claims, 1 Drawing Sheet

U.S. PATENT DOCUMENTS

| | | |
|---|---|---|
| 6,551,817 B2 | 4/2003 | Besemer et al. |
| 6,613,529 B2 | 9/2003 | Bedilion et al. |
| 2002/0047003 A1* | 4/2002 | Bedingham et al. ........ 219/388 |
| 2002/0192701 A1 | 12/2002 | Adey |
| 2003/0087292 A1 | 5/2003 | Chen et al. |
| 2003/0104494 A1 | 6/2003 | Ravkin et al. ............... 435/7.9 |
| 2003/0123322 A1* | 7/2003 | Chung et al. ............ 366/165.1 |

OTHER PUBLICATIONS

Williams, P.T. et al., "Catalytic pyrolysis of tyres: influence of catalyst temperature", Fuel, IPC Science and Technology Press, Guildford, Great Britain, vol. 81, No. 18, Dec. 2002, pp. 2425-2434, XP004380934.

* cited by examiner

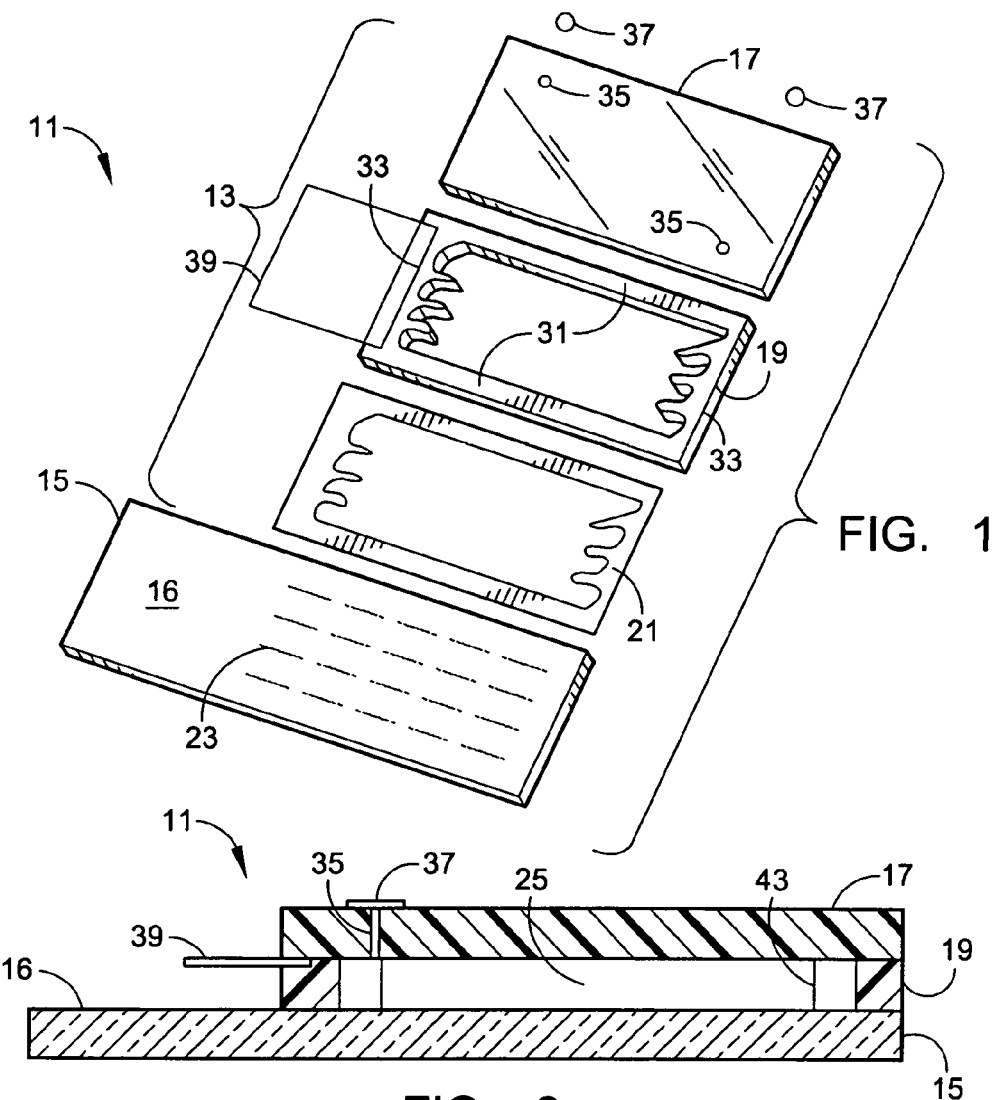
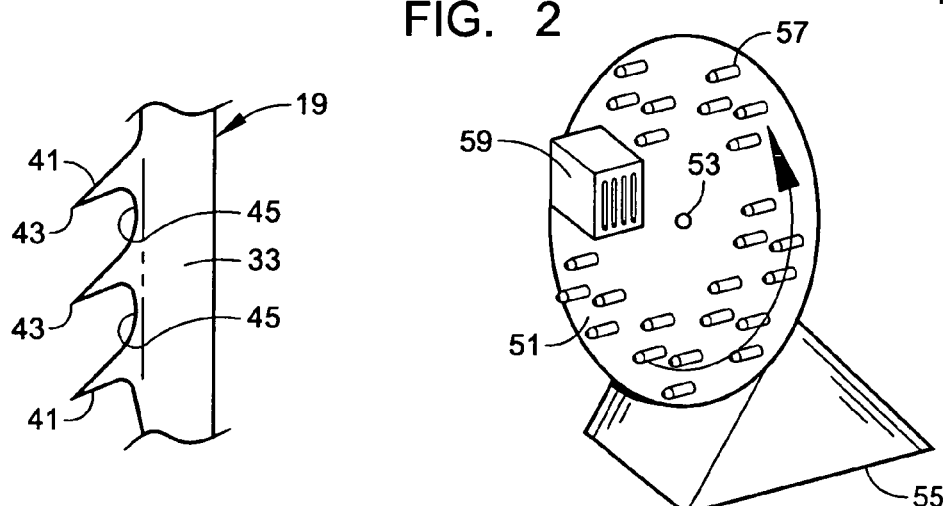

MICROARRAY HYBRIDIZATION DEVICE HAVING BUBBLE-FRACTURING ELEMENTS

FIELD OF THE INVENTION

This invention relates to devices for effectively and efficiently carrying out hybridization of microassays using only relatively small amounts of the target solution and more particularly to improved devices of the type referred to generally as gasket-type or gasketed hybridization chambers which are designed to achieve thorough mixing in such a chamber containing a microassay with only 50 or a few hundred microliters of target solution.

Hybridization of microarrays is frequently carried out by exposing "probe" molecules bound to a microscope slide surface to a solution of "target" molecules. There are presently four mainstream methods for hybridizing microarrays in this general way; they are referred to as coverslips, gasketed hybridization chambers, microscope slide mailers, and automated hybridization instruments. Choice of which method to implement often depends on factors such as probe and/or target availability, reagent and hardware costs, performance requirements, and user expertise.

The coverslip method is used when target volumes are limited to a few microliters per slide. A few drops of target are deposited onto a slide, and a thin glass or plastic coverslip is placed on top of the target. The capillary action between coverslip and slide traps a thin film of target solution.

When working with intermediate volumes, a gasket-type hybridization chamber, such as one of those commercially available from Grace Biolabs, Schleider and Shuel, or MWG-Biotech, is often used. A cover and gasket are provided, with the gasket having a thickness greater than the liquid film of the coverslip method. The gasket is usually attached to the slide with adhesive which it carries. A transparent cover formed with or without target solution injection ports is attached to the top surface of the gasket. These hybridization chambers usually accommodate, but are not limited to, volumes of 50 µl to 800 µl. Hybridization in these gasket-type chambers may take place with (dynamic) or without (static) agitation of the target solution.

Hybridization of microarrays with volumes of 1 ml and greater is often performed in mailers, staining jars, or similar products. In this method, slides are placed into containers with enough target solution to envelop the entire slide on both sides. The containers may then be agitated or left static during the hybridization reaction.

Automated hybridization machines have a variety of different designs, capacities, and agitation mechanisms, but they are similar in that, in each machine, slide temperature, volume, agitation, and sequence of hybridization and wash steps is preprogrammed and requires minimal user interaction.

BACKGROUND OF THE INVENTION

Microarray technology is a significant tool presently being used to promote progress in research in numerous fields including genomics and proteomics. This technology has broad applications to life science research, pharmaceutical and biotechnology R & D, and molecular and clinical diagnostics. Hybridization reactions between nucleic acids (or other biological moieties) are fundamental to microarray applications. These in vitro reactions will usually transpire between biological probes (oligonucleotide, cDNA, RNA, PNA, peptide, protein, etc.) bound to a solid support and free target (oligonucleotide, cDNA, RNA, PNA, peptide, protein, etc.) in solution. The probes and targets, regardless of their nature, are complementary and specific to each other. For example, for an oligonucleotide single strand probe, its target is the complementary single strand sequence. For a protein array, the target can be a protein (antigen) and its probe the target-specific antibody. Nucleic acid based microarrays are also capable of detecting specific mistakes in complementary sequences, such that a single base mismatch will significantly lower hybridization efficiency.

Hybridization of microarrays may be carried out under static conditions, without any external agitation of the hybridization target solution. Under these conditions, diffusion is limited to convection and is influenced by kinetic properties of the target (size, mobility, solution temperature) and viscosity of hybridization solution. In general, hybridization kinetics under static conditions are slow, and the resulting hybridizations become time-consuming and unpredictable. Diffusion in this case is not an entirely reliable process, which may result in decreased sensitivity and specificity of the array. Further inconsistencies in the microarray hybridization process may result from variations in array heating and orientation.

The coverslip method is generally always used with static conditions because the capillary action created by the coverslip prevents any convective solution motion. This method is preferred when the amount of target solution is limited. It involves placing a few microlitters of highly concentrated target solution onto a microarray and placing a glass or plastic coverslip directly on top of the target. The target solution then spreads into a thin layer, via capillary action, between the coverslip and the slide. Such restricted space, as available between the coverslip and slide, allows limited if any fluid movement in the film layer itself. In addition, evaporation of target solution has been known to occur, resulting in drying and precipitation of target onto the slide, and this can cause further inconsistency as well as scanning artifacts. For most dependable and consistent microarray measurements, environmental conditions and temperatures must be very strictly controlled during hybridization.

When large target volumes are available, hybridization can be carried out using mailers, staining jars, or even conical centrifuge tubes. Efficient agitation of the liquid volumes in these containers can be accomplished by rocking, shaking, etc. Properly performed, this causes thorough movement of the target solution across the microarray and results in uniform hybridization across the surface of the slide(s). Though hybridization in mailers is usually efficient and consistent when done properly, the method requires the consumption of a large volume of (perhaps expensive) target solution.

Gasket-based hybridization chamber experiments are typically carried out with a relatively small target solution volume (50-800 µl). One shortcoming of this type of hybridization chamber has been that agitation of the target solution via movement of the slide and hybridization chamber (rotation, shaking, etc.) is often insufficient to counteract the force of capillary action inherent in these hybridization chambers; therefore, sufficient mixing is often not achieved so as to produce consistency of hybridization throughout the microarray. A method for improving agitation within the chamber utilizes injection of an air bubble into the target solution, see e.g. U.S. Pat. No. 6,613,529 (Sep. 2, 2003); subsequent movement of the slide and chamber during hybridization then causes the solution to be displaced by the movement of the bubble to effect better mixing throughout the hybridization chamber. Although such a bubble mechanism provides internal mixing, unfortunately such mixing is very often not uniform across the surface of the slide. When the device is attached to a shaker (vortexer), the bubble may get trapped at one end of the chamber. Devices attached to rockers or orbital rotators (where the slide moves in a windmill like motion) may also experience problems with uniformity. In a rocker, a bubble travels up and down the surface of the slide carrying the microarray but generally follows one particular path; in an orbital rotator, the bubble moves along the inner edge of the hybridization chamber, again often following one particular path and not mixing the solution efficiently in the center region of the slide. Attempts to overcome such difficulties are described in U.S. Pat. No. 6,485,918 and in patent application Publications Ser. Nos. 2002/192,701 and 2003/87,292.

A final method to actively agitate a hybridization solution in such a reaction is via the use of automated hybridization stations. The design, capacity, and agitation mechanisms of the various commercial offerings vary. However, such hybridization stations typically cost $30,000 to $60,000, which is often cost prohibitive.

These problems are felt to be even more problematic in hybridization of 3-dimensional (3D) microarrays compared to two-dimensional (2D) microarrays; probes in such 3D microarrays are immobilized within a three-dimensional hydrogel polymer droplet (90-98% solvent), which in turn is attached to a solid support. Typically the support is a chemically functionalized glass microscope slide, though it could be any other type of solid or semi-permeable material, e.g. plastic, silicon, membrane, or metal. The number of probe-containing spots can range anywhere from 1 to 10,000. The plurality of probe spots which constitute the microarray are then exposed to target material diluted in liquid buffer to detect for hybridization. During hybridization, the target must diffuse to and into each spot to reach its complementary probe. Even for 2D arrays, the target has to be delivered to the location of the probe on the surface, and non-binding target needs to be carried away from all non-complementary probes. Therefore, adequate agitation of the target solution is critical to the efficiency and consistency of microarray hybridization reactions. Experimental conditions including temperature of hybridization, target and probe concentrations, and the rate of target delivery to and from the immobilized probes are also important. This last factor is greatly influenced by the degree to which the target solution is mixed during the hybridization reaction. Solutions that are well mixed yield consistent hybridization results, while solutions that are poorly mixed tend to be irreproducible as well as possibly having artifacts introduced.

After hybridization is complete, microarrays usually undergo a wash step; then they are dried and are scanned using a data collection device. These devices are generally confocal laser scanners, CCD (charge coupled device) cameras systems or fluorescent microscopes. The scanner emits a monochromatic light beam, which excites fluorophores bound to the microarray. The resultant emission is then filtered, collected by a photomultiplier tube (PMT), and converted to numerical intensity values. The greater the signal intensity, the greater the degree of hybridization for that particular probe/target system. Often, microarray results can be negatively influenced or even ruined by streaks, splotches, or high background on the microarray. These artifacts are typically caused by inadequate blocking prior to hybridization, inadequate solution mixing during hybridization or improper washing after hybridization.

To obviate the above-mentioned difficulties, the search has continued for improved hybridization devices.

SUMMARY OF THE INVENTION

A novel approach has been developed for generating sufficient and consistent mixing of small target solution volumes within a hybridization chamber. Unlike conventional bubble methods that utilize one or a few relatively large bubbles; this approach utilizes a multitude of much smaller bubbles which greatly increase the degree of mixing and uniformity of the hybridization reaction across the surface of the entire microarray. The cost is equivalent to other gasket-based hybridization chambers, and the volume of target solution used in the hybridization chamber is also similar.

In these improved devices, microbubbles are generated though the use of bubble fracturing elements that may take the form of teeth-like projections that protrude or project laterally into the interior volume of the hybridization chamber. As the devices are manipulated, large bubbles break up into microbubbles when they encounter such bubble fracturing elements in their path. As a result of such creation of microbubbles, there are far greater numbers of possible paths for bubbles to follow as result of movement of the device, and this leads to better solution mixing across the surface of the microarray. It is believed that the plurality of paths along which these microbubbles travel assure the amount of internal agitation of the target solution that is desired for thorough hybridization in a chamber which typically holds target solution in a volume of from 50 μl to 800 μl.

In one particular aspect, a microarray hybridization device which comprises a flat substrate having a surface to which a microarray of reactive moieties can be attached, liquid barrier means juxtaposed with said surface to create a chamber in which said microarray is located, and means closing said chamber so said device may be manipulated without loss of liquid target solution that fills said chamber except for a gaseous bubble included therein, said barrier means having inwardly facing surfaces which border said chamber, which surfaces are formed with a plurality of bubble-fracturing elements that extend laterally into said chamber so that, when said device is moved so that a liquid target solution in said chamber moves along said surface from one boundary of said chamber to another boundary, a bubble initially in said chamber is ruptured into a plurality of microbubbles that then assure very effective distribution of the liquid target solution in said chamber across the entire microarray, driven by movement of said microbubbles.

In another particular aspect, a method of effecting hybridization between probes and a target solution, which method comprises providing a flat substrate having a surface to which a microarray of reactive probe moieties are attached, juxtaposing a perimeter liquid barrier with said surface to create a chamber, in which said microarray is located, and closing said chamber so said substrate may be manipulated without loss of liquid target solution, filling said chamber with a target solution and a gaseous bubble, and moving said substrate to cause the target solution to move from one boundary of said chamber to another with at least one such boundary being shaped so that as a result of such movement the bubble in said chamber is ruptured into a plurality of microbubbles that then assure very effective distribution of the liquid target solution across the entire microarray, driven by subsequent movement of such microbubbles.

In yet another particular aspect, a cover and gasket subassembly for forming a microarray hybridization device with a substrate having a microarray on a surface thereof, which subassembly comprises a flat cover having an upper and lower surface, a perimeter barrier of rectangular shape affixed to said lower surface of said cover, pressure-sensitive adhesive upon an undersurface of said perimeter barrier for attachment of said cover to the surface of the substrate so as to surround the microarray, and a release sheet covering said adhesive, said barrier having inwardly facing surfaces which border said chamber, which surfaces are formed with a plurality of bubble-fracturing elements that extend laterally into said chamber so that, when said device is moved so that a liquid target solution in said chamber moves along said surface from one boundary of said chamber to another boundary, a bubble initially in said chamber is ruptured into a plurality of microbubbles.

BRIEF DESCRIPTION OF THE DRAWINGS

FIG. 1 is an exploded perspective view showing a glass slide in a combination with a cover and gasket subassembly designed to construct a microarray hybridization device having various features of the invention.

FIG. 2 is a side view, enlarged in size, showing the microarray hybridiziation device assembled from the components of FIG. 1.

FIG. 3 is an enlarged fragmentary plan view of a section of the gasket shown in FIG. 1.

FIG. 4 is a schematic of a device for manipulating the filled device of claim 2 during hybridization incubation.

DETAILED DESCRIPTION OF THE PREFERRED EMBODIMENT

Illustrated in FIGS. 1 to 3 is an example of a microarray hybridization device 11 embodying various features of the present invention. Shown are the components of a cover and gasket subassembly 13 which bind to a glass slide 15 or the like to create a sealed hybridization chamber; the subassembly includes a flat cover 17 and a peripheral gasket 19.

The glass slide 15 provides a flat substrate upon which a microarray can be attached. Although the substrate 15 may be a standard glass laboratory slide, any other flat surface-providing object could be used that would be suitable for carrying biological samples. For example, they could be made of polymeric material instead of glass or any other suitable impervious material to which probe-carrying microdots might be applied. A standard laboratory slide 15 may be rectangular in shape having dimensions of 1×3 in. Of course other sizes and/or shapes could be used, but standardization is desirable for microassay hybridization reactions. Generally, thickness of the substrate is immaterial so long as the surface is impervious.

The cover 17 of the subassembly may be a rectangular sheet of liquid-impermeable material that provides a flat upper surface for the hybridization chamber, to which surface there is fixed the perimeter or peripheral gasket 19. The gasket that may have the same exterior dimensions as the cover so that its edges are essentially coplanar. Although the cover-gasket subassembly might be a single piece, for the economies of manufacture, it is preferably made in separate pieces which are then suitably joined together by any suitable means, as by adhesive, solvent bonding, heat sealing or the like. For example, both the cover 17 and the gasket 19 may be made of polymeric material and suitable joined as by high strength adhesive.

For example, covers might be simply cut from a sheet of polycarbonate or polypropylene or polyethylene or some other polymeric material that is preferably hydrophobic, so as not to attract an aqueous hybridization target solution injected into the chamber which is formed once the subassembly has been mated with the glass slide or other substrate. The cover may be transparent, and for some applications preferably is optically clear. However, for other applications, for instance those which are light-sensitive, the cover may preferably be opaque.

The gasket 19 can be simply die-cut from suitable sheet material or molded in quantity as by injection molding. It may also be made from polymeric material, and it may be formed of the same polymer as the cover or a compatible polymer, so long as the material is liquid impervious as to provide a liquid-tight type chamber in which the hybridization incubation reaction can take place. It is preferably also formed by hydrophobic material. For example, the gasket 19 may be die-cut from a closed cell polymeric foam material having a high strength pressure-sensitive adhesive on one surface so that it can be easily laminated or otherwise affixed to the undersurface of the cover 17.

The subassembly is designed to be subsequently preferably adhesively adjoined to the flat substrate that carries the microarray, and to facilitate such, it is preferred that the undersurface of the gasket 19 be provided with a layer of pressure-sensitive adhesive and covered by a release liner 21. The release liner 21 might only cover the adhesive surface of the gasket 19, or it may be rectangular in shape, essentially the same dimensions as the cover, so that it seals the entire surface of the chamber and assures cleanliness. In the former arrangement, it would be die cut at the same time the gasket 19 is die cut from stock material. The cover 17 may be stiff or have flexibility, and the gasket 19 material may be of a like character. Because following most hybridizations it will be desirable to remove the gasketed cover so as to wash and then treat or analyze the microarrays, the cover 17 is preferably flexible to facilitate its peeling from the substrate.

In operation, once a microarray 23 has been applied to the upper surface of the glass slide 15, it is ready for the attachment of the subassembly 13 to create the hybridization incubation device. Accordingly, the release liner 21 is simply carefully stripped from the undersurface of the adhesive-bearing gasket 19, and the gasketed cover is carefully mated with the slide by generally aligning three edges surfaces to create the device shown in FIG. 2 where a reaction chamber 25 is formed that is bounded by the upper surface 16 of the glass slide, the undersurface of the cover 17 and the interior surfaces of the walls of the gasket 19, with the gasket now being sealed to the facing flat substrate 16 and cover 17. The liquid-tight chamber 25 wherein the microarray 23 is located is then filled with a liquid target solution.

Examining the gasket 19 more closely, it can be seen that it serves as a peripheral barrier in the form of two parallel long walls 31 and two short walls 33 which are perpendicular thereto that form a rectangular reaction chamber after the subassembly 13 has been laminated onto the glass slide 19. The cover 17 contains a pair of apertures or openings 35, preferably located near opposite ends of the chamber, that facilitate the filling of the chamber through one aperture 35 and the escape of air through the other aperture 35 at the opposite end. The cover 17 preferably carries a tab 39 that facilitates its being peeled from the slide after the incubation period has ended. Although the tab may be an integral part of the cover 17, as by being an extension of one edge that extends past the gasket 19 or a die-cut projection that extends outward from the rest of the edge of the cover, it is preferably affixed to the undersurface of the cover, as illustrated in FIG. 2, and extends along the end of the glass slide where the microarray is not located. It may be made of stiff or flexible material and firmly attached by adhesive, heat- or solvent-bonding or the like. The cover 17 and tab 39 are preferably both flexible to facilitate peeling following incubation. The device is designed to be used by incompletely filling the chamber with the hybridization target solution so as to leave an air bubble, the purpose of which is to promote mixing during the movement of the device while the hybridization reactions are taking place. Once the filling is completed, the apertures 35 are closed in any suitable manner, as by applying plugs or adhesive seals 37 that simply fit over the apertures and prevent any leakage.

As earlier indicated, the movement of a large bubble within the reaction chamber while somewhat promoting mixing is not considered to be truly effective, and the gasket or the peripheral barrier 19 is constructed with a plurality of bubble-fracturing elements 41 that extend into the reaction chamber 25 from the surfaces of the shorter pair of walls 33. These bubble-fracturing elements 41 are preferably hydrophobic and are formed as triangular fingers with sharp edges 43 at their tips which, upon engagement with a bubble in the aqueous solution, cause the splitting of the bubble into two separate bubbles of smaller volume. As a result, as the continuous manipulation of the target solution-filled device continues, likely over several hours time, the initial bubble and its progeny are split time and time again, creating a multitude of microbubbles in the aqueous solution that are spread essentially uniformly across the width of the interior of the reaction chamber as they move end to end as the device is being manipulated as described hereinafter.

The sharp edges 43 extend between the two facing, flat surfaces of the glass slide 15 and the cover 17, and they are aligned essentially perpendicular thereto. Pocket regions 45 are located between the bubble-fracturing elements 41, and they accommodate and promote the formation of the microbubbles. Depending upon how the filled devices are to be rotated, it may be desirable to construct or aim the bubble-fracturing elements 41 so that they point toward the general direction from which the bubbles will be rising in the chamber as they approach the shorter wall 33. If the manipulation would be such that the bubbles would be approaching the walls 33 in a direction essentially perpendicular thereto, the bubble-fracturing elements 41 might be pointed directly outward from the interior wall surface. In the illustrated arrangement, they are oriented or aligned at an angle of about 45° from the adjacent wall surface, pointing toward the lower interior wall surface of the longer wall 31 against which the bubbles may rise when rotating the device in the plane of the glass slide itself, which arrangement may be preferred. With such an orientation wherein the bubble-fracturing elements 41 are pointed toward the rising streams of bubbles, there is a greater propensity for the bubbles to split upon their engagement with the sharp edges 43.

Illustrated in FIG. 4 is an example of one type of apparatus that might be used to continuously rotate or manipulate the target solution-filled devices during incubation, which may extend for a period of, for example, 6-18 hours. Depicted is a support wheel 51 supported on a generally horizontal axle 53 and driven from a support base 55 that contains an electric motor that causes the rotation of the axle and the wheel at a desired speed, preferably between about 2-20 rpms, e.g. about 8 rpms. One or both surfaces of the wheel contain a plurality of supports 57 that are designed to accept a cartridge 59 containing a plurality of the target solution-filled hybridization devices 11, thus facilitating the incubation of multiple test samples at one time. Of course, other supports on the same wheel, if desired, could be configured to accept individual devices not supported in a cartridge 59. The arrangement is preferably such that the devices 11 are slowly rotated in the plane thereof so the bubbles tend to generally rise along the one long wall 31 on the high side of the chamber.

Although the invention has been described with regard to certain preferred embodiments which constitutes the best mode presently known for carrying out the invention, it should be understood that various modifications and changes as would be obvious to one having the ordinary skill in this art may be made without departing from the scope of the invention that is defined in the claims appended hereto. The disclosures of all U.S. patents mentioned herein are expressly incorporated herein by reference.

Particular features of the invention are emphasized in the claims that follow.

The invention claimed is:

1. A microarray hybridization device which comprises:
a flat substrate having a surface to which a microarray of reactive moieties can be attached,
liquid barrier means juxtaposed with said surface to create a chamber having an interior wall surface in which chamber said microarray is located, and
a cover closing said chamber so said device may be manipulated without loss of liquid target solution that fills said chamber except for a gaseous bubble included therein,
said barrier means having inwardly facing surfaces which border said chamber and which are generally perpendicular thereto, which surfaces are formed with a plurality of bubble-fracturing elements that lie in a planar region extending parallel to said flat substrate and extend laterally into said chamber so that, when said device is moved so that a liquid target solution in said chamber moves along said flat substrate surface from one boundary of said chamber to another boundary, a bubble initially in said chamber is ruptured into a plurality of microbubbles that then assure very effective distribution of the liquid target solution in said chamber across the entire microarray, driven by movement of said microbubbles.

2. The microarray hybridization device of claim 1 wherein said cover is flat and is spaced uniformly from said surface by said barrier means.

3. The microarray hybridization device of claim 2 wherein said cover is made of substantially rigid, transparent material.

4. The microarray hybridization device of claim 2 wherein said barrier means has a height such as to space said cover between about 0.2 and about 2 mm from said surface.

5. The microarray hybridization device of claim 2 wherein said barrier means forms a generally rectangular perimeter of said chamber having four walls and wherein one or more of the four walls of said barrier means includes sharp edges that are aligned substantially perpendicular to said surface upon which the microarray is attached, which edges are spaced apart by pockets and function as said bubble-fracturing elements.

6. The microarray hybridization device according to claim 5 wherein said bubble-fracturing elements are disposed along two opposed boundary walls of said rectangular perimeter barrier and are formed by a plurality of generally triangular fingers that project from boundary walls into said chamber and have said sharp edges at the tips thereof, with said pockets being located therebetween.

7. The microarray hybridization device according to claim 6 wherein said rectangular perimeter includes two longer walls and two shorter walls with said bubble-fracturing elements being formed as part of said two shorter walls.

8. The microarray hybridization device according to claim 7 wherein said triangular fingers in said two shorter walls are aligned so as to project in the direction from which bubbles in the target solution in said chamber will normally approach the respective wall when the device moved during hybridization.

9. The microarray hybridization device according to claim 2 wherein said bubble-fracturing elements are formed of hydrophobic material.

10. The microarray hybridization device according to claim 2 wherein said cover is made of an opaque hydrophobic material and includes at least one filling port through which said liquid target solution can be supplied into said chamber wherein a microarray is disposed.

11. A microarray hybridization device which comprises:
a flat substrate having an upper surface,
a microarray of reactive moieties attached to said upper surface,
a liquid perimeter barrier juxtaposed with said surface to create a chamber having an interior wall surface, in which chamber said microarray is located, and
a cover juxtaposed with said barrier to close said chamber so said device may be manipulated without loss of a liquid target solution that fills said chamber except for a gaseous bubble included therein,
said perimeter barrier having inwardly facing walls which border said chamber and which are generally perpendicular thereto, which walls are formed with a plurality of bubble fracturing elements that lie in a planar region extending parallel to said flat substrate and extend laterally into said chamber so that, when said device is moved so that the liquid target solution moves along said flat substrate surface upon which said microarray is located, a bubble initially in said chamber is ruptured into a plurality of microbubbles that assure very effective distribution of the liquid target solution in said chamber across the entire microarray, driven by movement of said microbubbles.

12. The microarray hybridization device of claim 11 wherein said cover is flat, being made of substantially rigid, transparent material, and is spaced uniformly between about 0.2 and about 2 mm from said surface by said perimeter barrier.

13. The microarray hybridization device of claim 12 wherein said perimeter barrier forms a generally rectangular chamber and wherein one or more of the four walls thereof includes protrusions having sharp edges that are aligned substantially perpendicular to said surface on which said microarray is located, said protrusions being spaced apart by pockets and functioning as said bubble-fracturing elements.

14. The microarray hybridization device according to claim 12 wherein said cover includes at least one filling port through which said liquid target solution can be supplied into said chamber and wherein said microarray includes a plurality of 3D spots which are attached to said upper surface and extend upward therefrom about 20 μm, which 3D spots carry said reactive moieties.

15. A method of effecting hybridization between probes and a target solution, which method comprises:

providing a microarray hybridization device according to claim 1 containing a microarray of reactive probe moieties,
filling the chamber of said device with a target solution and a gaseous bubble, and
moving said substrate to cause the target solution to move from one boundary of said chamber to another with at least one such boundary being shaped so that as a result of such movement the bubble in said chamber is ruptured into a plurality of microbubbles that then assure very effective distribution of the liquid target solution across the entire microarray, driven by subsequent movement of such microbubbles thereby increasing the degree of mixing and hybridization.

16. The method of claim 15 wherein said chamber is formed and closed by a flat cover and a depending perimeter gasket that spaces said cover uniformly from said surface.

17. The method of claim 16 wherein said gasket forms a generally rectangular perimeter of said chamber having two opposed shorter walls and wherein said microbubbles are created by sharp-edged protrusions that project into said chamber from said two opposed shorter walls in the direction from which a bubble would approach each said wall during normal movement.

18. The method according to claim 17 wherein said target solution is introduced through at least one filling port in said cover which is then sealed.

19. The method of claim 17 wherein said substrate is moved by rotation about an axis which is substantially horizontal and wherein said chamber is aligned so that said shorter walls are generally perpendicular to a line extending radially from said axis of rotation.

20. A microarray hybridization device which comprises:
a flat substrate having an upper surface,
a microarray of reactive moieties in 3D spots attached to said upper surface,
a rectangular liquid perimeter barrier juxtaposed with said surface to create a chamber in which said microarray is located,
a flat cover juxtaposed with said barrier to close said chamber so as to confine a liquid target solution therein that fills said chamber except for a gaseous bubble,
said cover including at least one filling port through which a liquid target solution can be supplied into said chamber, and
means for sealing said port so said device may be manipulated in a substantially vertical plane about a horizontal axis without loss of the confined target solution,
said perimeter barrier having four inwardly facing surfaces which border said chamber and which are generally perpendicular thereto, which surfaces are formed with a plurality of bubble-fracturing elements that extend laterally into said chamber in a planar region between said cover and said flat substrate, so that, when said device is manipulated causing the liquid target solution to move along said flat substrate surface upon which said microarray is located, a bubble initially in said chamber is ruptured into a plurality of microbubbles that assure very effective distribution of the liquid target solution in said chamber across the entire microarray, driven by movement of said microbubbles.

21. The microarray hybridization device of claim 20 wherein said bubble-fracturing elements comprise generally triangular protrusions having sharp edges, that are aligned substantially perpendicular to said surface on which said microarray is located, which elements are located on one or more of four walls which form said perimeter barrier, said generally triangular protrusions being spaced apart by pockets.

22. The microarray hybridization device according to claim 21 wherein said protrusions are located on two shorter walls of said four walls of said rectangular barrier and wherein said plurality of 3D spots which are attached to said upper surface extend upward therefrom at least about 20 µm.

* * * * *